United States Patent [19]

Groth et al.

[11] Patent Number: 5,610,255

[45] Date of Patent: Mar. 11, 1997

[54] PROCESS FOR PREPARING POLYSUCCINIMIDE AND POLYASPARTIC ACID

[75] Inventors: Torsten Groth; Winfried Joentgen, both of Köln; Nikolaus Müller, Monheim; Ulrich Liesenfelder, Köln, all of Germany

[73] Assignee: Bayer AG, Leverkusen, Germany

[21] Appl. No.: 516,811

[22] Filed: Aug. 18, 1995

Related U.S. Application Data

[63] Continuation-in-part of Ser. No. 195,321, Feb. 14, 1994, abandoned.

[30] Foreign Application Priority Data

Feb. 22, 1993 [DE] Germany .......................... 43 05 368.8
May 6, 1993 [DE] Germany .......................... 43 14 965.0
Jun. 8, 1993 [DE] Germany .......................... 43 19 044.8

[51] Int. Cl.$^6$ .................. C08F 120/58; C08F 122/02

[52] U.S. Cl. ................ 526/304; 526/318.2; 526/240

[58] Field of Search ................ 526/304, 318.2, 526/240

[56] References Cited

U.S. PATENT DOCUMENTS

| 5,116,513 | 5/1992 | Koskan et al. | 210/698 |
|---|---|---|---|
| 5,288,783 | 2/1994 | Wood | 525/418 |
| 5,393,868 | 2/1995 | Freeman et al. | 528/480 |

*Primary Examiner*—Joseph L. Schofer
*Assistant Examiner*—Wu C. Cheng
*Attorney, Agent, or Firm*—Connolly & Hutz

[57] ABSTRACT

Polysuccinimide and polyaspartic acid are prepared by polymerizing maleic anhydride, ammonia and water or maleic acid derivatives or fumaric acid derivatives in bulk or dissolved in solvents in a continuous kneading reactor. The polysuccinimide formed can be converted into polyaspartic acid and polyaspartate salts by hydrolysis.

10 Claims, No Drawings

PROCESS FOR PREPARING POLYSUCCINIMIDE AND POLYASPARTIC ACID

Cross-Reference to Related Application

The present application is a continuation-in-part of U.S. application Ser. No. 08/195,321 filed on Feb. 14, 1994 now abandoned. The entire disclosure of Ser. No. 08/195,321 is expressly incorporated herein by reference.

The invention relates to a process for preparing polysuccinimide and polyaspartic acid and salts thereof by reaction of maleic anhydride derivatives, particularly at temperatures of from 120° C. to 200° in an extruder.

The preparation and use of polyaspartic acid (PAA) and derivatives thereof has long been the subject of numerous publications and patents. Thus the preparation can be via thermal polycondensation of aspartic acid (J. Org. Chem. 26, 1084 (1961)).

U.S. Pat. No. 4 839 461 (=EP-A 0 256 366) describes the preparation of polyaspartic acid from maleic anhydride, water and ammonia. Maleic anhydride is converted into the monoammonium salt in aqueous medium by addition of concentrated ammonia solution. The monoammonium salt is melt-polymerized to polysuccinimide and hydrolysed to PAA or PAA salts.

It is known from U.S. Pat. No. 4 590 260 (=JP-A 1984(59)-60160) that amino acids together with derivatives of malic, maleic and/or fumaric acid can be subjected to a polycondensation at from 100° to 225° C. According to U.S. Pat. No. 4 696 981 microwaves are used in such reactions.

DE-A 2 253 190 (=U.S. Pat. No. 3 846 380) describes a process for preparing polyamino acid derivatives, specifically polyaspartic acid derivatives. According to this patent maleic acid derivatives (monoammonium salt and monoamide) as well as aspartic acid are used in a thermal polymerization to prepare the intermediate polysuccinimide, which can then be reacted with amines in suitable solvents to give the desired derivatives: see Examples 2 to 4 therein.

Polyaspartic acid can, according to EP-A 256 366 (U.S. Pat. No. 4 839 461), be used for scale inhibition and scale deposit removal in water. According to U.S. Pat. No. 5 116 513 and EP-A-454 126 polyaspartic acid and salts thereof are active components of detergents and fertilizers.

The invention provides a process for preparing polysuccinimide and polyaspartic acid from maleic acid anhydride, ammonia and water or maleic acid derivatives such as the monoammonium salt or monoamide, and also the corresponding fumaric acid derivatives or mixtures of monoammonium maleate/diammonium maleate or of maleic monoamide/monoammoniummaleate, characterized in that the starting materials are subjected to a thermal, optionally continuous, polymerization at from 120° C. to 200° C. in a reactor with a residence time of in particular from 0.5 to 300 minutes and the product obtained is optionally converted by hydrolysis into polyaspartic acid or a salt thereof.

In a particularly preferred embodiment, the invention provides an improved process for preparing polysuccinimide and polyaspartic acid from the stated starting materials, characterized in that the starting materials are continuously polymerized, in bulk or dissolved in suitable solvents, in a continuous kneading reactor, preferably self cleaning and preferably one of non-extruder type, particularly preferably heated at temperatures from 120° to 200° C., preferably from 120° to 180° C., particularly preferably from 150° C. to 180° C., and residence times from 0.5 to 300 minutes, preferably from 1 to 90 minutes, in particular from 2 to 20 minutes, and the polysuccinimide obtained is optionally converted into polyaspartic acid or salts thereof by hydrolysis.

Non-extruder type continuous kneading reactors are distinct from extruder-type reactors by a large volume per unit throughput (allowing removal of large amounts of vapour), by low shear forces and the independence of axial conveying from the mixing actions of the rotors.

In the particularly preferred embodiment of the heated kneading reactor both the rotor(s) and the jacket can be heated from the inside, preferably by a heat transfer medium which ensures maintenance of a constant temperature. Furthermore, heating by various independent heating circuits can be considered, whereby different temperature zones in the reactor can be produced, enabling the carrying out of temperature ramps.

In another preferred embodiment the starting material firstly is heated up and partly polymerized, for example for at least 10% conversion of the starting material, in a tubular reactor, preferably a multi spiral tube reactor and the reaction mixture is then fed in the continuous kneading reactor.

In the present invention polyaspartic acid is taken to mean both the free polyaspartic acid and also salts thereof.

The polysuccinimide prepared according to the invention contains, in a preferred embodiment, essentially recurring succinimide units having the following structure:

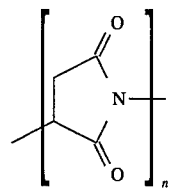

Additionally, by means of appropriate reaction procedure and choice of starting materials, further recurring units can be incorporated, for example a) aspartic acid units of the formula β-form

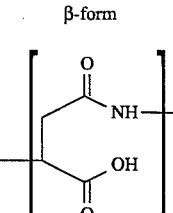

and

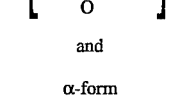

α-form

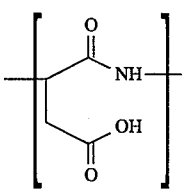

b) malic acid units of the formula

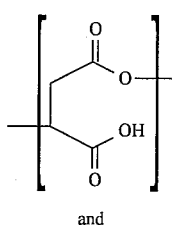

and

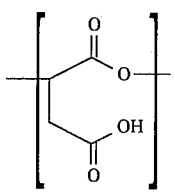

c) maleic acid and fumaric acid units of the formula

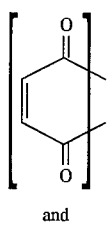

and

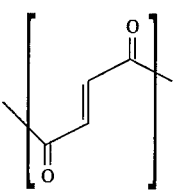

The polyaspartic acid prepared according to the invention contains, in a preferred embodiment, essentially those recurring units specified under a), in general at least 50 % being present in the β-form, and optionally the further structures specified above.

The analysis of the chemical structure is carried out preferably using $^{13}C$ NMR and, after total hydrolysis, using HPLC, GC and GC/MS.

The starting materials to be used according to the invention such as, for example, maleic monoamide or ammonium maleate can be prepared in a separate process and polymerized as dry pure materials, in solution or in mixtures having a lower melting point.

The starting materials can be converted into a polymerization product (polysuccinimide) by means of a thermal polymerization in a suitable reactor which can be operated batchwise (paddle dryer) or continuously (single-shaft and twin-shaft high-viscosity reactors, for example Disco-therm and All-Phasen-Konti machines from List, screw machines, preferably self-cleaning multi-shaft screw machines, or a belt-type reactor) with a residence time from 0.5 to 300 minutes, preferably from 1 to 60 minutes, at a temperature from 150° to 180° C. (preferably 160° to 180° C.) optionally in vacuo; the polymerization product can be converted into the corresponding salt of polyaspartic acid by dissolution in a base.

In particular, use may be made of all high-viscosity reactors which allow the water vapour liberated to be conducted away, preferably ones with large reaction volumes, also preferably ones with kinematic self-cleaning of the surfaces coming into contact with the product and likewise preferably ones with heating of the shafts. For reasons of corrosion resistance, machines made of corrosion resistant material, for example stainless steel, are preferably used.

For example an ORP-reactor, a CRP-reactor or an AP CONTI-reactor by LIST AG, CH 4422 Arisdorf, Switzerland, can be used.

These LIST reactors are large volume continuous mixing/kneading reactors for thermal processes with highly viscous or pasty products as well as solids which go through a sticky, pasty phase during processing.

Two parallel rotors work intermeshing in a figure-of-eight shaped barrel. The rotors are equipped with radially mounted disks, which can be heated and which carry the kneading bars. The rotors are counter-rotating at a rate ratio of about 1:4. The kinematic movement, shape and placement of the kneading bars are designed to provide cleaning of the opposite rotor and at the same time to produce intensive mixing and kneading. The intensive mixing action is mostly independent of axial transport. That means that the rate of rotation can be chosen in order to optimize the mixing and kneading action with only few influence on the mean residence time. Typically these reactors are operated at 40 to 75% filling, so that large amounts of gas and vapor can be distracted.

It is advantageous to feed the crude solution obtained by reaction of maleic anhydride, ammonia and water directly into the above-described high-viscosity reactors. The crude solution used can have an ammonium maleate content of 50% and above. It is advantageous here that dewatering and polymerization take place simultaneously. The water has two functions. It acts as a solvent and supports the particularly good heat transfer properties of the abovementioned reactors. The polymerization temperature is thereby appreciably lowered and the reaction can be carried out at temperatures between 120° C. and 180° C., preferably from 140° C. to 155° C. The water can be completely removed during polymerization. The result is a dry pulverulent material which consists predominantly of polysuccinimide. A variant comprises leaving part of the water in the reaction mixture. The result is then, depending on the residual water content, a viscous mass or a solution which comprises a mixture of polyaspartic acid and polysuccinimide in varying proportions. This variant has the advantage that the product obtained is appreciably more readily soluble in water and thus allows a simpler conversion to the salt. The maleic acid derivatives have a residence time in the above-described reactors of from 0.5 to 300 minutes, preferably from 1 to 90 minutes, particularly preferably from 2 to 20 minutes. The polymerization products are converted by dissolution in a base or in an aqueous solution and preferably at a pH-value from 12 to 6 at from 20° to 95° C., preferably from 40° to 70° C., particularly preferably from 50° to 70° C., into the corresponding polyaspartic acid salt. It is also possible to obtain the free polyaspartic acid already at this point by hydrolysis in water at 80°–100° C. or by treatment of the salt with acids or acid ion exchangers. The product is obtained as a fine powder by spray drying.

The salts prepared according to this process (e.g. sodium salt) have the properties of a dispersant and sequestering agent and of a corrosion inhibitor and can be employed correspondingly. Furthermore, an antimicrobial activity, i.e. against fungi and bacteria, can be demonstrated.

Analysis by gel permeation chromatography shows the polymer prepared to have different chain-lengths and molecular weights as a function of the reaction conditions, for example residence time and temperature of the thermal polymerization. ($M_w=$500 to 10,000, preferably 1000 to 5000, particularly preferably 2000 to 4000).

The compounds of the invention were used, in particular, as dispersants, detergent additives, sequestering agents, scale inhibitors, corrosion inhibitors especially for brass, as microbicides and in fertilizers.

EXAMPLE

The polymerization reaction was carried out in a AP 12 CONTI pilot plant reactor by LIST AG, CH-4422 Arisdorf, Switzerland.

The AP 12 CONTI is a twin rotor machine with heated rotors and barrels. The total heated surface is 1.17 m². The total reactor volume is 30.6 1. The maximum drive power is 5.5 kW and the rotors can be rotated at rates between 22 and 110 rpm. The reactor is discharged via a discharge twin screw. The reactor is equipped with two outgassing ports for the removal of vapors.

Preparation of polysuccinimide from an aqueous solution of monoammonium maleate 7480 g of 25% strength $NH_3$ solution (110 mol) were added at 60° C. to a mixture of 9800 g (100 mol) of maleic anhydride and 2825 g of $H_2O$ over a period of one hour. A suspension of the monoammonium salt of maleic acid in water was obtained. At temperatures above 70° C. this suspension became a homogeneous solution having a solids content of about 67%. This solution was metered into the mixing part of the LIST machine heated to from 170° C. to 185° C. at a rate of 5 kg/h. In the mixing part a smooth evaporation of the solution water immediately began and one obtained a viscous liquid. Upon being conveyed through the reactor under kneading and mixing the reaction mixture changed from a viscous liquid to a coarse grained product, which was removed from the reactor by a screw conveyor. The reaction mixture had a retention time in the reactor which was between 60 minutes and 75 minutes. One obtained 2415 g/h of a light orange product.

Characterization of the product obtained

To characterize the product, acid number, elemental composition and molecular weight distribution were determined. Furthermore, applicational tests in respect of the sequestering and dispersing action of the product were carried out.

TABLE 1

| Elemental composition | |
|---|---|
| C [% by weight] | 46.5 |
| H [% by weight] | 3.7 |
| N [% by weight] | 13.3 |
| $NH_4$ [% by weight] | 1.1 |
| $H_2O$ [% by weight] | 0.3 |
| Molecular weight distribution by GPC Mw | 3080 |
| Acid number (mg (NaOH)/g) | 405 |

Preparation of sodium polyaspartate 30 g =about 0.28 mol of the polysuccinimide/polyaspartic acid mixture obtained is suspended in about 50 ml of $H_2O$ and dissolved at about 60° C. with 50% strength sodium hydroxide solution until a pH of 8.5–9.0 is reached. The solution is concentrated in vacuo and the sodium polyaspartate obtained is completely dried. About 38 g are obtained.

Applicational tests carried out after conversion into the sodium salt:

a) Sequestration of a surfactant

Testing of the turbidity of a sodium alkylbenzenesulphonate solution in tap water (total water hardness: 14 degrees of German hardness).

1 ml of a 10 % strength solution of a surfactant customarily used in detergents and based on an alkylbenzenesulphonic acid (Marlon®A 375) is admixed with 0.1 g of sodium polyaspartate and made up to 100 ml with tap water. The solution obtained is stable for over three weeks. Without the addition of sodium polyaspartate the solution becomes turbid in a few minutes.

b) Dispersion of zinc oxide 0.3 g of sodium polyaspartate are dispersed in 200 ml of tap water together with 10 g of zinc oxide. The dispersion is transferred to a measuring cylinder. After three hours, samples are taken from different positions in the measuring cylinder and analysed for their zinc oxide content. It was found that the zinc oxide content is always the same as a result of the good dispersing action. Furthermore, the sedimentation stability was determined after 3 hours and 24 hours. In both cases, practically no layer of sediment was found at the bottom of the measuring cylinder.

In addition to the applicational tests the biodegradability of the product was tested according to the test procedures of the OECD guide lines for testing of chemicals (1981). The product showed a biodegradation of 70% after 28 days according to the OECD 301E test protocol.

A SCAS test was also conducted following the OECD 302 A test protocol. The product showed an average degradation rate of 76% for a 28 day test period.

What is claimed is:

1. Process for preparing polysuccinimide or polyaspartic acid, wherein a starting material which is selected from the group consisting of monoammonium maleate, diammonium maleate, mixtures of monoammonium maleate and diammonium maleate, monoammonium fumarate, diammonium fumarate and mixtures of monoammonium fumarate and diammonium fumarate; is subjected to a continuous thermal polyermization at from 120° C. to 200° C. in a continuous kneading reactor of the non-extruder type with a residence time of from 0.5 to 300 minutes to form said polysuccinimide and, optionally, subjecting said polysuccinimide to hydrolysis to form said polyaspartic acid or salts thereof.

2. Process according to claim 1, wherein the starting materials are continuously polymerized in bulk or in solution in said continuous kneading reactor.

3. Process for preparing polyaspartic acid or salts thereof, which comprises preparing polysuccinimide in accordance with the process of claim 1 and then hydrolyzing said polysuccinimide.

4. Process according to claim 1, wherein the starting materials used are monoammonium maleate, diammonium maleate or mixtures of the two formed from maleic acid anhydride, ammonia and water.

5. Process according to claim 1, wherein the polymerization is carried out at from 150° C. to 180° C.

6. Process according to claim 1, wherein the polymerization is carried out at from 1 to 90 minutes.

7. Process for preparing a salt of polyaspartic acid, which comprises preparing polysuccinimide in accordance with the process of claim 1 and then hydrolyzing said polysuccinimide by treating it with water at a pH from 12 to 6.

8. Process according to claim 1, in which the polymerization is carried out in the presence of a compound which lowers the melting point of the reaction mixture.

9. A process according to claim 1, wherein the starting material is monoammonium maleate, diammonium maleate or mixtures of the two formed from maleic acid and ammonia.

10. Process for preparing polysuccinimide or polyaspartic acid, wherein a mixture of maleic acid anhydride, ammonia and water is subjected to a continuous thermal polymerization at from 120° C. to 200° C. in a continuous kneading reactor of the non-extruder type with a residence time of from 0.5 to 300 minutes to form said polysuccinimide and, optionally, subjecting said polysuccinimide to hydrolysis to form said polyaspartic acid or salts thereof.

* * * * *